United States Patent
Asano et al.

(10) Patent No.: US 7,943,177 B2
(45) Date of Patent: May 17, 2011

(54) POLYAMIDE POROUS SPHERICAL PARTICLE

(75) Inventors: Yukihiko Asano, Chiba (JP); Tatsuya Shoji, Chiba (JP); Shigeru Yao, Chiba (JP)

(73) Assignee: Ube Industries, Ltd., Ube-shi, Yamaguchi (JP)

(*) Notice: Subject to any disclaimer, the term of this patent is extended or adjusted under 35 U.S.C. 154(b) by 539 days.

(21) Appl. No.: 12/088,112

(22) PCT Filed: Sep. 25, 2006

(86) PCT No.: PCT/JP2006/318997
§ 371 (c)(1), (2), (4) Date: Mar. 26, 2008

(87) PCT Pub. No.: WO2007/037211
PCT Pub. Date: Apr. 5, 2007

(65) Prior Publication Data
US 2009/0246235 A1    Oct. 1, 2009

(30) Foreign Application Priority Data
Sep. 27, 2005 (JP) .................. 2005-280211

(51) Int. Cl.
*C08L 77/00* (2006.01)
*C08L 77/02* (2006.01)
*A61K 9/14* (2006.01)

(52) U.S. Cl. .................. 424/489; 424/401; 525/432

(58) Field of Classification Search .................. 424/401, 424/489
See application file for complete search history.

(56) References Cited

U.S. PATENT DOCUMENTS
2006/0127424 A1    6/2006    Asano et al.

FOREIGN PATENT DOCUMENTS
| JP | 2002 080629 | | 3/2002 |
| JP | 2005 120203 | | 5/2005 |
| JP | 2005 239575 | | 9/2005 |
| WO | WO 2004/043411 | * | 3/2004 |

OTHER PUBLICATIONS

International Search Report Application No. PCT/JP2006/318997 mailed on Nov. 21, 2006.
English Translation of International Preliminary Report on Patentability—Application No. PCT/JP2006/318997 dated Apr. 1, 2008.
English Translation of Written Opinion of the International Searching Authority—Application No. PCT/JP2006/318997 dated Apr. 1, 2008.

* cited by examiner

*Primary Examiner* — Gina C Yu
(74) *Attorney, Agent, or Firm* — Nixon Peabody LLP; Jeffrey L. Costellia

(57) ABSTRACT

Polyamide porous spherical particles having a number-average particle diameter of 2 to 30 μm, a BET specific surface area of 100 to 80,000 m²/kg, and a ratio of a volume-average particle diameter to the number-average particle diameter in the range of 1.52 to 2.50 is reduced in luminous reflectance.

5 Claims, No Drawings

POLYAMIDE POROUS SPHERICAL PARTICLE

FIELD OF THE INVENTION

The present invention relates to polyamide porous spherical particles (powder). The invention further relates to cosmetic compositions containing the polyamide porous spherical particles as components.

BACKGROUND OF THE INVENTION

Japanese Patent Provisional Publication No. 2002-80629 discloses polyamide porous spherical particles having pores on their surfaces which have a number-average particle diameter of 1 to 30 µm, a BET specific surface area of 100 to 80,000 m²/kg, and a ratio [PDI (particle diameter distribution index)=Dv/Dn] of a volume-average particle diameter (Dv) to the number average particle diameter (Dn) in the range of 1 to 1.5.

The above-mentioned publication describes that the polyamide porous spherical particles can be used for carriers of catalysts, toners of electrophotography, electronics materials of display devices, chromatography, adsorbents in food industries, and medical technology.

WO 2004/043411 describes cosmetic composition utilizing polyamide porous spherical particles which have a number-average particle diameter of 1 to 30 µm, a BET specific surface area of not less than 5 m²/g, a boiled linseed oil-absorbing amount of not less than 200 mL/100 g, a crystallinity (measured by DSC) of not less than 40%, and a particle diameter distribution index of 1.0 to 1.5. This publication describes that the polyamide porous spherical particles are effective for reducing abnormal light-scattering on human skin and shielding defective appearances on human skin such as fine wrinkles and depressions.

SUMMARY OF THE INVENTION

In the cosmetic compositions containing polyamide porous spherical particles, the reduction of abnormal light-scattering on human skin and the shielding of defective appearances on human skin such as fine wrinkles and depressions can be effectively achieved by reducing reflectance (luminous reflectance) of the polyamide porous spherical particles. However, the reduction of luminous reflectance has not been heretofore studied on the polyamide porous spherical particles.

Accordingly, it is the object of the present invention to provide polyamide porous spherical particles which show reduced luminous reflectance.

The present inventors have discovered that polyamide porous spherical particles having a certain number-average particle diameter and a particle diameter distribution index (a ratio of a volume-average particle diameter to a number-average particle diameter) in the range of 1.52 to 2.50 shows less luminous reflectance than polyamide porous spherical particles having the essentially same number-average particle diameter and a particle diameter distribution index in the range of 1.0 to 1.5. The present invention has been made on the basis of this discovery.

The present invention resides in polyamide porous spherical particles (powder) having a number-average particle diameter of 2 to 30 µm, a BET specific surface area of 100 to 80,000 m²/kg, and a ratio of a volume-average particle diameter to the number average particle diameter in the range of 1.52 to 2.50.

The preferred embodiments of the polyamide porous spherical particles are described below.

(1) The polyamide porous spherical particles have a spherulite structure.

(2) The polyamide porous spherical particles have a porosity index in the range of 5 to 60.

(3) The polyamide porous spherical particles have a mean pore diameter in the range of 0.01 to 0.5 µm.

(4) The polyamide porous spherical particles have a void volume in the range of 30 to 70%.

(5) The polyamide porous spherical particles comprise polyamide 6.

The invention further resides in a cosmetic composition comprising polyamide porous spherical particles having a number-average particle diameter of 2 to 30 µm, a BET specific surface area of 100 to 80,000 m²/kg, and a ratio of a volume-average particle diameter to the number-average particle diameter in the range of 1.52 to 2.50 dispersed in a cosmetic base material.

In the cosmetic composition of the invention, the polyamide porous spherical particles preferably have a spherulite structure.

The polyamide porous spherical particles of the invention show less luminous reflectance than the conventional polyamide porous spherical particles. Therefore, the cosmetic composition containing the polyamide porous spherical particles of the invention are favorably employable for reducing abnormal light-scattering on human skin and shielding defective appearances on human skin such as fine wrinkles and depressions.

PREFERRED EMBODIMENTS OF THE INVENTION

The polyamide porous spherical particles of the invention have a BET specific surface area of 100 to 80,000 m²/kg, preferably 1,000 to 60,000 m²/kg, more preferably 3,000 to 40,000 m²/kg.

The polyamide porous spherical particles of the invention have a number-average particle diameter of 2 to 30 µm, preferably 2 to 25 µm, more preferably 4 to 20 µm, most preferably 5 to 9 µm. If the number-average particle diameter is lower than the above-mentioned range, the polyamide porous spherical particles are apt to aggregate and hence handling is not easy. If the number-average particle diameter is greater than the above-mentioned range, the luminous reflectance increases.

The polyamide porous spherical particles of the invention have a particle diameter distribution index (Dv/Dn) of 1.52 to 2.50, preferably 1.55 to 2.20, more preferably 1.60 to 2.20. The particle diameter distribution index means a ratio (Dv/Dn) of a volume-average particle diameter (Dv) to the number-average particle diameter (Dn).

The particle diameter distribution index shows extent of the particle diameter distribution of the polyamide porous spherical particles. As the particle diameter distribution index approaches 1, the extent of the particle diameter distribution of the polyamide porous spherical particles narrows. If the particle diameter distribution index of the polyamide porous spherical particles is less than the above-mentioned range, the polyamide porous spherical particles show higher luminous reflectance. On the contrary, if the particle diameter distribution index of the polyamide porous spherical particles is more than the above-mentioned range, segregation caused by variation of particle diameters likely occurs. Particularly, it may be difficult to disperse the polyamide porous spherical particles uniformly in a liquid cosmetic composition, if the particle diameter distribution index is too great. This is because the great particle diameter distribution index means that the distribution of the particle diameter is extended widely, and the sedimentation velocities of the polyamide porous spherical particles having the widely extended particle diameter distribution vary greatly.

The number-average particle diameter (Dn) and volume-average particle diameter (Dv) can be obtained by measuring the particle diameters of the polyamide porous spherical particles and then placing the measured value in the below-mentioned formulas:

$$Dn = \sum_{i=1}^{n} Xi/n$$

$$Dv = \sum_{i=1}^{n} Xi^4 / \sum_{i=1}^{n} Xi^3$$

[in the above-mentioned formulas, Xi means the measured particle diameters of the polyamide porous spherical particles, and n is the number of the measured polyamide porous spherical particles].

It is preferred that each of the polyamide porous spherical particles of the invention has a spherulite structure. The polyamide porous spherical particles show a high light-scattering property due to a combination of the spherulite structure and porous structure. In this invention, the description to the effect that each of the polyamide porous spherical particles has a spherulite structure means that each particle has a spherulite structure that is characteristic in the crystalline polymer particle formed in such manner that polymer fibrils grow radially or three-dimensional-isotopically from a single nucleus or plural nuclei positioned in or near the central area of the particle. The fact that the particle has a spherulite structure can be confirmed by observation using a transmission electron microscope (TEM) or observation of light transmission under crossed nicols using a polarization microscope.

The polyamide porous spherical particles of the invention have a porosity index (RI) preferably in the range of 5 to 60, more preferably in the range of 5 to 50. The porosity index (RI) means a ratio of BET specific surface area [RI=S/S$_o$] in which S is a BET specific surface area of the polyamide porous spherical particles and S$_o$ is a BET specific surface area of non-porous spherical polyamide particles having smooth surface and the same number-average particle diameter. The S$_o$, that is, a BET specific surface area of non-porous spherical polyamide particles having smooth surface and the same number-average particle diameter, can be obtained using the following formula:

$$S_0(m^2/kg)=6/[\rho(kg/m^3) \times Dn(m)]$$

[in which ρ is a density of polyamide, and Dn is a number-average particle diameter].

The polyamide porous spherical particles of the invention have a mean pore diameter preferably in the range of 0.01 to 0.5 μm, more preferably in the range of 0.01 to 0.3 μm, further preferably in the range of 0.01 to 0.2 μm, most preferably in the range of 0.02 to 0.1 μm.

The polyamide porous spherical particles of the invention have a void volume preferably in the range of 30 to 70%, more preferably in the range of 30 to 60%. The void volume means a ratio of the volume of voids to the whole volume of the polyamide porous spherical particle (total of the volume of the polyamide and the volumes of voids) and can be obtained using the following formula:

$$\text{Void volume}(\%)=100 \times P(m^3/kg)/[P(m^3/kg)+ 1/\rho(m^3/kg)]$$

[in the formula, P is an accumulated volume of pores formed in the polyamide porous spherical particles, and ρ is the density of polyamide].

The polyamide porous spherical particles of the invention have a melting temperature preferably in the range of 110 to 320° C., more preferably 140 to 280° C.

The polyamide porous spherical particles of the invention have a crystallinity of preferably not less than 40%, more preferably not less than 50%. The crystallinity can be obtained using the following formula:

Crystallinity(%)=100×[Amount of heat of fusion (J/g) measured on polyamide porous spherical particles by means of a differential scanning calorimeter (DSC)/Amount of heat of fusion (J/g) determined on polyamide having a crystallinity of 100%]

The polyamide porous spherical particles of the invention may comprise aliphatic polyamides, alicyclic polyamides, aromatic polyamides, or their copolymer polyamides. Preferred are aliphatic polyamides. Examples of the aliphatic polyamides include homopolymers such as polyamide 6, polyamide 66, polyamide 11 and polyamide 12, and their copolymer polyamides. More preferred are such as polyamide 6 and polyamide 66, and their copolymer polyamides. The polyamide preferably contains carboxyl groups at the terminal in greater numbers relative to amino groups.

The polyamide forming the polyamide porous spherical particles of the invention preferably has a number-average molecular weight in the range of 3,000 to 50,000, more preferably in the range of 5,000 to 20,000.

The polyamide porous spherical particles of the invention can be prepared by mixing a polyamide solution, a non-solvent for the polyamide and water to temporarily form a uniform mixture solution and subsequently precipitate polyamide particles.

The polyamide solution has a polyamide concentration of preferably in the range of 0.1 to 30 wt. %, more preferably 0.2 to 25 wt. %. Examples of the solvents employable for preparing the polyamide solution include aromatic alcohols, formic acid, and mixtures thereof. Examples of the aromatic alcohols include phenol, o-cresol, m-cresol, p-cresol, and chlorophenol. The polyamide solution can contain a freezing point depressant. The freezing point depressant can be the non-solvent for polyamide or water, provided that the incorporation of the non-solvent or water does not cause precipitation of polyamide in the polyamide solution.

The non-solvent for polyamide can be compatible (slightly soluble) with the solvent for polyamide (aromatic alcohol or formic acid) and water. Examples of the non-solvents for polyamide include aliphatic alcohols, aliphatic ketones and mixtures thereof. Examples of the aliphatic alcohols include methanol, ethanol, 1-propanol, 2-propanol, 1-butanol, 2-butanol, 2-methyl-1-propanol, 2-methyl-2-propanol, 1-pentanol, 1-hexanol, ethylene glycol, triethylene glycol, propylene glycol and glycerol. Examples of the aliphatic ketones include acetone and methyl ethyl ketone.

In the preparation of the polyamide porous spherical particles, the polyamide solution, non-solvent and water can be mixed in optional orders under the condition that the resulting mixture temporarily forms a uniform solution. For instance, for the preparation of the polyamide porous spherical particles, the following processes can be optionally performed:

1) the non-solvent is added to the polyamide solution, and subsequently water is added;

2) the non-solvent is mixed with water, and subsequently the polyamide solution is added; and 3) water is added to the polyamide solution, and subsequently the non-solvent is added.

The mixture of the polyamide solution, non-solvent for polyamide, and water can be prepared by batch system or continuous system.

In the preparation of the temporarily uniform mixture solution according to batch system, it is preferred that one weight part of the polyamide solution is mixed with 4.0 to 12.0 weight parts (total amount) of the non-solvent and water (more preferably 5.0 to 10.0 weight parts, most preferably 6.5 to 10.0 weight parts). As for amounts of the non-solvent and water, one weight part of the non-solvent is preferably mixed with 0.05 to 1.00 weight part of water (more preferably 0.10 to 0.80 weight part of water).

In the preparation according to the batch system, the period of procedures (mixing period) from the start of mixing of the polyamide solution, non-solvent and water to the finish of the mixing preferably completes within 30 to 300 seconds, more preferably within 45 to 120 seconds. If the mixing period is shorter than the above-mentioned range, the resulting polyamide porous spherical particles likely show less particle diameter distribution index. On the contrary, if the mixing period is longer than the above-mentioned range, the resulting polyamide porous spherical particles likely show extremely large particle diameter distribution index.

The mixture solution can be stirred in order to adjust the period from the completion of mixing of the polyamide solution, non-solvent and water to the formation of a uniform mixture solution.

After the formation of the uniform mixture solution from the polyamide solution, non-solvent and water, the solution is not stirred and allowed to stand for a period of 0.1 sec. to 240 min. (preferably 1 sec. to 120 min.), until the polyamide particles precipitate. The uniform mixture solution is preferably kept at 5 to 60° C. until the polyamide particles precipitate.

In the preparation of the temporarily uniform mixture solution according to continuous system, it is preferred that one weight part of the polyamide solution is mixed with 5.0 to 13.0 weight parts (total amount) of the non-solvent and water (more preferably 6.5 to 12.0 weight parts, most preferably 7.0 to 11.0 weight parts). As for amounts of the non-solvent and water, one weight part of the non-solvent is preferably mixed with 0.10 to 0.70 weight part of water, more preferably 0.15 to 0.60 weight part of water, most preferably 0.45 to 0.60 weight part).

The procedure for continuously mixing the polyamide solution, non-solvent and water can be performed in a mixing tank or a tubular mixer. The mixing tank can be equipped with a stirrer. The tubular mixer can be a static mixer or a screw extruder.

In the continuous procedure, it is preferred that the uniform mixture solution formed temporarily in a continuous mixing apparatus is transferred into a reservoir and allowed stand, for instance, for 0.1 sec. to 240 min. (preferably 1 sec. to 120 min.) until the polyamide particles precipitate. The transferring of the uniform mixture solution from the continuous mixture to the reservoir is preferably complete within 30 to 300 sec., more preferably within 30 to 90 sec.

In the preparation of the polyamide porous spherical particles, the precipitated polyamide particles can be recovered from the solution by conventional manners such as decantation, centrifugal separation and filtration. For instance, the polyamide particles can be recovered by adding an aliphatic alcohol (such as methanol, ethanol, or isopropanol) to the solution containing the precipitated polyamide particles and performing decantation or centrifugal separation. The precipitated polyamide particles can be washed with several portions of methanol or acetone and then recovered by decantation or centrifugal separation. The recovered polyamide particles can be subjected to hot air drying, spray drying, stirring drying or vacuum drying.

The polyamide porous spherical particles of the invention are favorably employable as materials for cosmetic compositions such as foundation. The cosmetic compositions containing the polyamide porous spherical particles of the invention are further described below.

The cosmetic composition according to the invention comprises the polyamide porous spherical particles of the invention dispersed in the cosmetic materials. The term of cosmetic materials means components for forming the cosmetic composition. Examples of the cosmetic materials include oily medium, aqueous medium, powdery medium, polymer medium for the preparation of packs, surface active agents functioning as emulsifying agent, and their mixtures.

The oily medium can be oil, wax, hydrocarbon, or a fatty acid. The aqueous medium can be purified water and a lower alcohol such as ethanol. The powdery medium can be an inorganic pigment such as talc or kaolin. The polymer medium can be natural polymer or synthetic polymer. The surface active agent can by a nonionic surfactant or an anionic surfactant.

The cosmetic material may further contain detergents, moisture-proof materials, softeners, styptic agents, UV ray cutters, colorants, perfumes, deodorants, thickers, preservatives, pH-adjusting agents, metal ion-chelating agents, cell-activators, blood circulation accelerators, whitening agents, sebum-reducing agents, bactericides, anti-inflammatory agents, and sweat depressants.

The cosmetic composition of the invention contains the polyamide porous spherical particles of the invention and can be applied to skin, lip, head skin, eye, nail, or hair. The cosmetic composition can be a cosmetic composition paste or a powder cosmetic composition. Otherwise, the cosmetic composition can be a cosmetic emulsion for applying skin.

The cosmetic composition of the invention preferably contains 1 to 60 wt. % of the polyamide porous spherical particles and 3 to 10 wt. % of an oily medium in the cosmetic composition.

Further, if the cosmetic composition of the invention is utilized as a colored cosmetic composition, the cosmetic composition preferably contains 1 to 60 wt. % of the polyamide porous spherical particles, 3 to 10 wt. % of an oily medium, and 1 to 30 wt. % of a colorant, in which the polyamide porous spherical particles are colored. In other words, the polyamide porous spherical particles can be employed in the form of particles colored with an organic colorant such as a colorant of red, green or yellow.

If the cosmetic composition of the invention is utilized as a foundation, the cosmetic composition preferably contains 1 to 10 wt. %, preferably 2 to 9 wt. %, of the polyamide porous spherical particles and 1 to 15 wt. % of an inorganic filler.

The cosmetic composition of the invention can be formulated for a cosmetic composition for a skin care purpose. In this case, the cosmetic composition preferably contains 5 to 20 wt. % of the polyamide porous spherical particles and 0.1 to 20 wt. %, preferably 0.2 to 15 wt. %, of a pharmaceutically active component.

If the cosmetic composition of the invention is employed for the skin care, the pharmaceutical effect of the pharmaceutically active component works efficiently and is maintained for a long time. In addition, the cosmetic composition effectively adsorbs sweat and secretion, whereby the cosmetic functions are kept for a long time. The pharmaceutically active component can be a known agent such as a defatting agent, a moisture-proofing agent, a decoloring agent, an uneven skin face-shielding agent, a skin softening agent, a skin disease-treating agent, or a perfumer.

The pharmaceutically active component is preferably held in the pores of the polyamide porous spherical particles. If the pharmaceutically active component is held in the pores of the polyamide porous spherical particles, the pharmaceutically active component is slowly released and the pharmaceutical effect is maintained for a long time.

The cosmetic composition for the foundation is applied to the skin directly, so as to smooth the uneven skin face and shield the defective or uneven skin, and shows affinity to the overcoating cosmetic composition as well as to the skin.

The cosmetic foundation composition can be prepared as cream, aqueous solution, emulsion, or gel.

The cosmetic foundation composition can contain the polyamide porous spherical particles and an inorganic filler, and if required, a fatty acid, an emulsion, silicone oil, a water-soluble polymer, a pigment, and a organic additive.

The fatty acid can be a saturated fatty acid or an unsaturated fatty acid or a derivative thereof. Examples of the saturated fatty acids include caprylic acid, lauric acid, myristic acid, palmitic acid, stearic acid, and their mixtures. Examples of the unsaturated fatty acids include palmitol acid, myristoleic acid, oleic acid, their mixtures, and poly-unsaturated fatty acids such as linoleic acid, linolenic acid and erucic acid. The fatty acid can be used in the form of a derivative such as a hydroxylated fatty acid or an esterified fatty acid.

The emulsion is preferably is a water-in-oil emulsion. The oil phase can comprise silicone oil, or non-silicone oils such as mineral oil, plant oil, bee wax, fat, and wax, or their mixtures.

The silicone oil can be volatile silicone oil or non-volatile silicone oil.

The inorganic filler can be titanium, silica, talc, kaolin, mica, or diatomaceous earth. The water soluble polymer can be polyvinyl alcohol, polyvinyl pyrrolidone, polyacrylic carboxylic acid and its derivative. The pigment can be an iron oxide pigment. The organic additive can be a moisture-proofing agent such as an amino acid or urea, perfumer, dye, or antiseptics. The oily medium can be paraffin, polyethylene wax, liquid paraffin, carnauba wax, plant oil, bee wax, silicone oil, or an aliphatic alcohol.

The cosmetic composition of the invention can contain an appropriate amount of inorganic pigments, dispersants, antiseptics, oxidation inhibitors, if needed.

The cosmetic composition can contain a water-soluble medium such as glycerol, ethylene glycol, propylene glycol, dipropylene glycol, 1,3-butylene glycol or sorbitol; an oily medium such as synthetic or natural oil such as fatty acid, fatty alcohol, wax (e.g., bee wax) or a derivative thereof, or synthetic or natural oil such as plant oil (e.g., camellia oil); an aqueous medium, and an emulsion, if necessary, in addition to the polyamide porous spherical particles. The aqueous medium can be water, or an alcohol such as ethanol. The cosmetic composition can further contain an inorganic powder (e.g., talc, clay), an organic powder, and a fibrous powder, so that they work for decreasing glittering, increasing brightness, adsorbing sweat, or decreasing peel-off.

The cosmetic composition can contain an active agent for treating acidic skin. Examples of the active agents include a β-lactam derivative, cyclofuroxasine, normal-furoxasine, tetracycline or its salt, erythromycin or its salt, or an extract such as an extract from plants.

The cosmetic composition of the invention preferably contains 10 to 300 weight parts of the liquid medium per 100 weight parts of the polyamide porous spherical particles. The liquid medium preferably is an oily medium or latex, such as volatile or non-volatile silicone oil, liquid paraffin, plant oil, wax, glycerol, or ethylene glycol.

The cosmetic composition of the invention can be formulated as a cleansing composition for washing the powdered skin.

EXAMPLES

In the following examples, the number-average particle diameter, volume-average particle diameter, particle size distribution index (i.e., ratio of the volume-average particle diameter (Dv) to the number-average particle diameter (Dn)), BET specific surface area, porosity index (RI), average pore diameter, void volume, crystallinity, and luminous reflectance were measured in the following manners.

[Number-Average Particle Diameter, Volume-Average Particle Diameter, and Particle Size Distribution Index]

The polyamide particles are dispersed in an electrolytic solution to give a dispersion. 50,000 polyimide particles in the dispersion is subjected to a Coulter counter to measure an equivalent circle diameter and calculate the number-average particle diameter, volume-average particle diameter, and particle size distribution index.

[BET Specific Surface Area]

The BET three-point measurement method using nitrogen absorption is utilized.

[Porosity]

The BET specific surface area measured as above is placed in the aforementioned formula to obtain the porosity. The polyamide 6 has a density of 1,180 kg/m$^3$.

[Average Pore Diameter]

The accumulated pore distribution in the pore diameter range of 0.0034 to 30 μm is measured by means of a mercury porosimeter to obtain the average pore diameter.

[Void Volume]

An accumulated pore volume is measured by a mercury porosimeter, and a graph of the accumulated pore volume against the pore diameters is prepared. An accumulated in-particle pore volume is obtained as an accumulated pore volume from the pore diameter at the greatest inflection point in the graph to a pore diameter smaller than that diameter by 0.035 μm. The accumulated in-particle pore volume is placed in the aforementioned formula to give the void volume. The polyamide 6 has a density of 1,180 kg/m$^3$

[Crystallinity]

The amount of heat of fusion of polyimide particles are measured by a differential scanning calorimeter (DSC) in a nitrogen stream at a flow rate of 40 mL/min., under the condition that the temperature elevation rate is set to 5° C./min. The amount of heat of fusion is placed in the aforementioned formula to give the crystallinity. The polyamide 6 having a crystallinity of 100% has an amount of heat of fusion of 189 J/g.

[Luminous Reflectance]

One weight part of an acrylic adhesive (acrylic resin: 11.9 wt. %, ethane dichloride: 64.4 wt. %, toluene: 27.3 wt. %) is diluted with toluene to give 1.5 weight parts of a diluted acrylic resin solution. Five weight parts of the polyamide particles are added to 95 weight parts of the diluted acrylic resin solution. The resulting mixture was subjected to ultrasonic processing to give a dispersion containing polyamide particles. The resulting dispersion is coated on a glass substrate by a doctor blade and dried at 100° C. to give a dispersion film having a thickness of 100 to 150 μm.

The dispersion film is placed in an angle-variable spectroscopic calorimeter Color Robot III (available from Color Techno System Co., Ltd.) to measure a luminar reflectance at a reflection angle of 45° detected upon receipt of an angle of incidence at 45°.

Example 1

Polyamide 6 (number-average molecular weight: 13000) was placed in a solution comprising phenol and methanol (9:1, ratio by weight) to prepare 15 kg of a polyamide 6 solution (polyamide concentration: 5 wt. %). The polyamide 6 solution was placed in a 200 L-volume reaction vessel equipped with a stirrer. While the polyamide 6 solution was stirred, a mixture (115 kg) comprising methanol (92 kg) and water (23 kg) was supplied to the stirred polyamide 6 solution for a period of 67 sec. at a constant rate by means of a liquid supply pump. After the supply of the mixture was complete, the resulting mixture comprising the polyamide solution, methanol and water was further stirred for 30 sec., to give a uniform mixture solution (solution temperature: 26° C.).

The mixture solution was allowed to stand, whereby polyamide 6 particles precipitated. After the precipitation of polyamide 6 particles was complete, the solution was allowed to stand for 60 min. The polyamide 6 particles in the mixture solution were recovered by means of a centrifugal separation apparatus. The recovered polyamide 6 particles were washed with hot methanol five times and spray-dried.

The obtained polyamide 6 particles were observed by means of a scanning electron microscope, and it was found that the particles were porous spherical particles. The polyamide 6 particles were then observed by means of a transmission electron microscope (TEM) on their sections. It was found that a crystalline structure was grown from the central nucleus and further that each particle had a spherulite structure. The polyamide 6 particles were further observed by means of a polarization microscope, and it was found that light was transmitted through the particles under cross nicols.

Thus, it was confirmed that the single polyamide 6 particle had a spherulite structure.

The polyamide 6 particles were subjected to measurements for the number-average particle diameter, volume-average particle diameter, particle diameter distribution index, BET specific surface area, porosity index, average pore diameter, void volume, crystallinity and luminous reflectance by the aforementioned procedures.

The following data were obtained: number-average particle diameter: 9.8 μm, volume-average particle diameter: 15.8 μm, particle diameter distribution index: 1.62, BET specific surface area: 18,100 $m^2$/kg, porosity index: 34.9, average pore diameter: 0.094 μm, void volume: 45%, crystallinity: 52%, luminous reflectance: 65.65%.

Example 2

Polyamide 6 (number-average molecular weight: 13000) was placed in a solution comprising phenol and methanol (9:1, ratio by weight) to prepare a polyamide 6 solution (polyamide concentration: 5 wt. %). The polyamide 6 solution and a mixture comprising methanol and water (weight ratio 2:1) were continuously supplied into a static mixer at flow rates of 100 g/min. for the polyamide 6 solution and 900 g/min. for the mixture, whereby the polyamide 6 solution, methanol, and water were mixed to give a uniform mixture solution. Portions of the mixed solution discharged from the static mixer were collected in reservoirs at every 60 sec. The mixed solution had a liquid temperature of 20° C.

The mixture solution was allowed to stand, whereby polyamide 6 particles precipitated. After the precipitation of polyamide 6 particles was complete, the solution was allowed to stand for 60 min. The polyamide 6 particles in the mixture solution were recovered by means of a centrifugal separation apparatus. The recovered polyamide 6 particles were washed with hot methanol five times and spray-dried.

The obtained polyamide 6 particles were observed by means of a scanning electron microscope, and it was found that the particles were porous spherical particles. The polyamide 6 particles were then observed by means of a transmission electron microscope (TEM) on their sections. It was found that a crystalline structure was grown from the central nucleus and further that each particle had a spherulite structure. The polyamide 6 particles were further observed by means of a polarization microscope, and it was found that light was transmitted through the particles under cross nicols.

Thus, it was confirmed that the single polyamide 6 particle had a spherulite structure.

The polyamide 6 particles were subjected to measurements for the number-average particle diameter, volume-average particle diameter, particle diameter distribution index, BET specific surface area, porosity index, average pore diameter, void volume, crystallinity and luminous reflectance by the aforementioned procedures.

The following data were obtained: number-average particle diameter: 6.7 μm, volume-average particle diameter: 11.2 μm, particle diameter distribution index: 1.67, BET specific surface area: 10,200 $m^2$/kg, porosity index: 13.4, average pore diameter: 0.090 μm, void volume: 40%, crystallinity: 50%, luminous reflectance: 52.96%.

Example 3

Polyamide 6 (number-average molecular weight: 13000) was placed in a solution comprising phenol and methanol (9:1, ratio by weight) to prepare 15 kg of a polyamide 6 solution (polyamide concentration: 10 wt. %). The polyamide 6 solution was placed in a 200 L-volume reaction vessel equipped with a stirrer. While the polyamide 6 solution was stirred, a mixture (115 kg) comprising methanol (92 kg) and water (23 kg) was supplied to the stirred polyamide 6 solution for a period of 100 sec. at a constant rate by means of a liquid supply pump. After the supply of the mixture was complete, the resulting mixture comprising the polyamide solution, methanol and water was further stirred for 30 sec., to give a uniform mixture solution (solution temperature: 28° C.).

The mixture solution was allowed to stand, whereby polyamide 6 particles precipitated. After the precipitation of polyamide 6 particles was complete, the solution was allowed to stand for 60 min. The polyamide 6 particles in the mixture solution were recovered by means of a centrifugal separation apparatus. The recovered polyamide 6 particles were washed with hot methanol five times and spray-dried.

The obtained polyamide 6 particles were observed by means of a scanning electron microscope, and it was found that the particles were porous spherical particles. The polyamide 6 particles were then observed by means of a transmission electron microscope (TEM) on their sections. It was found that a crystalline structure was grown from the central nucleus and further that each particle had a spherulite structure. The polyamide 6 particles were further observed by means of a polarization microscope, and it was found that light was transmitted through the particles under cross nicols.

Thus, it was confirmed that the single polyamide 6 particle had a spherulite structure.

The polyamide 6 particles were subjected to measurements for the number-average particle diameter, volume-average particle diameter, particle diameter distribution index, BET specific surface area, porosity index, average pore diameter, void volume, crystallinity and luminous reflectance by the aforementioned procedures.

The following data were obtained: number-average particle diameter: 10.6 μm, volume-average particle diameter: 22.6 μm, particle diameter distribution index: 2.13, BET specific surface area: 16,200 m$^2$/kg, porosity index: 32.6, average pore diameter: 0.104 μm, void volume: 47%, crystallinity: 46%, luminous reflectance: 65.80%.

Comparison Example 1

Polyamide 6 (number-average molecular weight: 13000) was placed in a solution comprising phenol and methanol (9:1, ratio by weight) to prepare 150 g of a polyamide 6 solution (polyamide concentration: 5 wt. %). The polyamide 6 solution was placed in a 2 L-volume reaction vessel equipped with a stirrer. While the polyamide 6 solution was stirred, a mixture (1,125 g) comprising methanol (900 g) and water (225 g) was supplied to the stirred polyamide 6 solution for a period of 20 sec. Just after when the supply of the mixture was complete, the stirring was terminated, to give a uniform mixture solution.

The mixture solution was allowed to stand, whereby polyamide 6 particles precipitated. After the precipitation of polyamide 6 particles was complete, the solution was allowed to stand for 60 min. The polyamide 6 particles in the mixture solution were recovered by means of a vacuum filtration apparatus. The recovered polyamide 6 particles were washed with hot methanol several times and spray-dried.

The obtained polyamide 6 particles were observed by means of a scanning electron microscope, and it was found that the particles were porous spherical particles. The polyamide 6 particles were then observed by means of a transmission electron microscope and a polarization microscope. It was confirmed that the single polyamide 6 particle had a spherulite structure.

The polyamide 6 particles were subjected to measurements for the number-average particle diameter, volume-average particle diameter, particle diameter distribution index, BET specific surface area, porosity index, average pore diameter, void volume, crystallinity and luminous reflectance by the aforementioned procedures.

The following data were obtained: number-average particle diameter: 9.1 μm, volume-average particle diameter: 9.95 μm, particle diameter distribution index: 1.10, BET specific surface area: 18,100 m$^2$/kg, porosity index: 26.8, average pore diameter: 0.091 μm, void volume: 48%, crystallinity: 51%, luminous reflectance: 71.55%.

The number-average particle diameter, particle diameter distribution index and luminous reflectance of the polyamide porous spherical particles obtained in Examples 1 to 3 and Comparison Example 1 are set forth in the following Table 1.

TABLE 1

| | Particle diameter (μm) | Distribution Index (-) | Luminous reflectance (%) |
|---|---|---|---|
| Example 1 | 9.8 | 1.62 | 65.65 |
| Com. Ex. 1 | 9.1 | 1.10 | 71.55 |
| Example 2 | 6.7 | 1.67 | 52.96 |
| Example 3 | 10.6 | 2.13 | 65.80 |

The data of Table 1 clearly indicate that the polyamide porous spherical particles having a higher particle diameter distribution index give a lower luminous reflectance as compared with the polyamide porous spherical particles having a substantially equal number-average particle diameter but a lower particle diameter distribution index.

In other words, the comparison of Example 1 and Comparison Example 1 having a substantially equal number-average particle diameter indicates that the polyamide porous spherical particles having a particle diameter distribution index within the range of the invention gives a lower luminous reflectance under the conventional measuring conditions (that is, the angle of incidence of light is the same as the angle of reflection), as compared with the polyamide porous spherical particles having a particle diameter distribution index lower than the range of the invention.

Example 4

To 5 weight parts of the polyamide porous spherical particles obtained in Example 1 were added the below-mentioned materials A to F, and water was added to give 100 weight parts of a mixture. The mixture was uniformly mixed to give a foundation cream. The obtained foundation cream was coated on a skin. When a light was applied to the coated skin, no light glittering was observed.

Material A: mixture of cyclomethicone (22 weight parts) and cetylmethicone (0.2 weight part)

Material B: mixture of mica (0.1 weight part), silica (1 weight part), titanium (7.5 weight parts) and zinc oxide (3.0 weight parts)

Material C: mixture of iron oxide black pigment (0.17 weight part), iron oxide red pigment (0.52 weight part) and iron oxide yellow pigment (1.82 weight parts)

Material D: mixture of trihydroxystearin (0.3 weight part) and cyclomethicone (1.0 weight part)

Material E: propyl p-hydroxybenzoate (0.75 weight part)

Material F: mixture of glycerol (8.0 weight parts), polyvinylpyrrolidone (0.5 weight part), sodium chloride (2.0 weight parts), sodium dehydroacetate (0.3 weight part), phenoxyethanol (0.25 weight part), and EDTA tetrasodium salt (1.0 weight part)

What is claimed is:

1. Polyamide porous spherical particles having a number-average particle diameter of 2 to 30 μm, a BET specific surface area of 100 to 80,000 m$^2$/kg, and a ratio of a volume-average particle diameter to the number-average particle diameter in the range of 1.52 to 2.50,
    wherein the polyamide porous spherical particles have a spherulite structure.

2. The polyamide porous spherical particles of claim 1, wherein the polyamide porous spherical particles have a porosity index in the range of 5 to 60.

3. The polyamide porous spherical particles of claim 1, wherein the polyamide porous spherical particles have a mean pore diameter in the range of 0.01 to 0.5 μm.

4. The polyamide porous spherical particles of claim 1, wherein the polyamide porous spherical particles have a void volume in the range of 30 to 70%.

5. The polyamide porous spherical particles of claim 1, wherein the polyamide porous spherical particles comprise polyamide 6.

* * * * *